US009283200B2

(12) United States Patent
Mohamed et al.

(10) Patent No.: US 9,283,200 B2
(45) Date of Patent: Mar. 15, 2016

(54) TREATMENT OF MEDIUM-CHAIN ACYL-COA DEHYDROGENASE DEFICIENCY

(71) Applicant: University of Pittsburgh-of the Commonwealth System of Higher Education, Pittsburgh, PA (US)

(72) Inventors: Al-Walid Mohsen Mohamed, Carnagie, PA (US); Gerard Vockley, Pittsburgh, PA (US)

(73) Assignee: University of Pittsburgh—of the Commonwealth System of Higher Education

( * ) Notice: Subject to any disclaimer, the term of this patent is extended or adjusted under 35 U.S.C. 154(b) by 0 days.

(21) Appl. No.: 14/515,298

(22) Filed: Oct. 15, 2014

(65) Prior Publication Data

US 2015/0216824 A1    Aug. 6, 2015

Related U.S. Application Data

(63) Continuation of application No. PCT/US2013/036739, filed on Apr. 16, 2013.

(60) Provisional application No. 61/624,864, filed on Apr. 16, 2012.

(51) Int. Cl.
*A61K 31/19* (2006.01)
*A61K 31/12* (2006.01)
*A61K 31/192* (2006.01)
*A61K 31/216* (2006.01)

(52) U.S. Cl.
CPC ............. *A61K 31/192* (2013.01); *A61K 31/216* (2013.01)

(58) Field of Classification Search
CPC .............................. A61K 31/19; A61K 31/12
USPC .................................................. 514/568, 679
See application file for complete search history.

(56) References Cited

U.S. PATENT DOCUMENTS

| 5,686,491 A * | 11/1997 | Sherwood ...................... 514/561 |
| 2006/0120971 A1* | 6/2006 | Crockford et al. ............... 424/46 |
| 2007/0123588 A1* | 5/2007 | Charles .......................... 514/547 |
| 2015/0216824 A1 | 8/2015 | Mohamed et al. |

OTHER PUBLICATIONS

Aoyama, et al., "Purification of Human Very-Long-Chain Acyl-Co-enzyme A Dehydrogenase and Characterization of Its Deficiency in Seven Patients" Journal of Clinical Investigation 95: 2465-2473, 1995.
Binzak, et al., "Identification of the catalytic residue of human shortrbranched chain acyl-CoA dehydrogenase by in vitro mutagenesis" Biochimica et Biophysica Acta 1382: 137-142, 1998.
Dixon, et al., "Intercurrent illness in inborn errors of intermediary metabolism", Archives of Disease in Childhood, 1992, vol. 67, pp. 1387-1391. See pp. 1389-1391.
Egger, et al., "Inhibition of Histone Deacetylation Does Not Block Resilencing of p16 after 5-Aza-2'-Deoxycytidine Treatment" Cancer Res 67:346-353, 2007.
Fernandes, et al., Inborn Metabolic Diseases: Diagnosis and Treatment, 4th Edition, Berlin: Springer, 2006, ISBN 978-3-540-28783-4. See pp. 83-85 and 94.
Finocchiaro, et al., "Molecular Cloning and Nucleotide Sequence of cDNAs Encoding the α-Subunit of Human Electron Transfer Flavoprotein" J. Biol. Chem. 263: 15773-80, 1988.
Finocchiaro, et al., "Purification and Properties of Short Chain Acyl-CoA, Medium Chain Acyl-CoA, and Isovaleryl-CoA Dehydrogenases from Human Liver" J. Biol. Chem. 262: 7982-9, 1987.
Frerman, et al., "Fluorometric Assay of Acyl-CoA Dehydrogenases in Normal and Mutant Human Fibroblasts" Biochem Med 33:38-44, 1985.
Ghisla, et al., "Mechanistic Studies with General Acyl-CoA Dehydrogenase and Butyryl-CoA Dehydrogenase: Evidence for the Transfer of the βHydrogen to the Flavin N(5)-Position as a Hydride" Biochemistry 23: 3154-3161, 1984.
Gore, et al., "Impact of the Putative Differentiating Agent Sodium Phenylbutyrate on Myelodysplastic Syndromes and Acute Myeloid Leukemia" Clinical Cancer Res 8:2330-2339, 2001.
Ikeda, et al., "[46] 2-Methyl Branched-Chain Acyl-CoA Dehydrogenase from Rat Liver" Enzymology 166: 374-89, 1988.
Ikeda, et al., "[47] Isovaleryl-CoA Dehydrogenase from Rat Liver" Methods in Enzymology 166: 374-89, 1988.
Ikeda, et al., "Purification and Characterization of Isovaleryl Coenzyme A Dehydrogenase from Rat Liver Mitochondria" J. Biol. Chem. 258: 1077-1085, 1983.
Ikeda, et al., "Purification and Characterization of Short-chain, Medium-chain, and Long-chain Acyl-CoA Dehydrogenases from Rat Liver Mitochondria" J. Biol. Chem. 260: 1311-1325, 1985.
Ikeda, et al. "Purification and characterization of 2-methyl-branched Chain acyl Coenzyme A dehydrogenase, an enzyme involved in isoleucine and valine metabolism, from Rat Liver Mitochondria" J Biol Chem 258:9477-9487, 1983.
Ikeda, et al. "Separation and Properties of Five Distinct Acyl-CoA Dehydrogenases from Rat Liver Mitochondria" J Biol Chem 258:1066-1076, 1983.
Ikeda, et al. "Spectroscopic Analysis of the Interaction of Rat Liver Short-Chain, Medium-Chain and Long-Chain Acyl-CoA Dehydrogenases with Acyl-CoA Substrates" Biochemistry 24: 7192-7199, 1985.
Ikeda, et al., "Mechanism of Action of Short-chain, Medium-chain, and Long-chain Acyl-CoA Dehydrogenases: Direct evidence for carbanion formation as an intermediate step using enzyme-catalyzed C-2 proton/deuteron exchange in the absence of C-3 exchange" J Biol Chem 260:1326-1337, 1985.

(Continued)

*Primary Examiner* — Raymond Henley, III
(74) *Attorney, Agent, or Firm* — Baker Botts, LLP

(57) ABSTRACT

The present invention provides for methods and compositions for treating medium chain acyl-CoA dehydrogenase deficiency. It is based, at least in part, on the discovery that phenylbutyrate can serve as a substrate for medium chain acyl-CoA dehydrogenase. In non-limiting embodiments, phenylbutyrate and/or another source of phenylacetate is administered as a chaperone treatment to patients suffering from medium chain acyl-CoA dehydrogenase deficiency.

12 Claims, 5 Drawing Sheets

(56) References Cited

OTHER PUBLICATIONS

Figure 1:
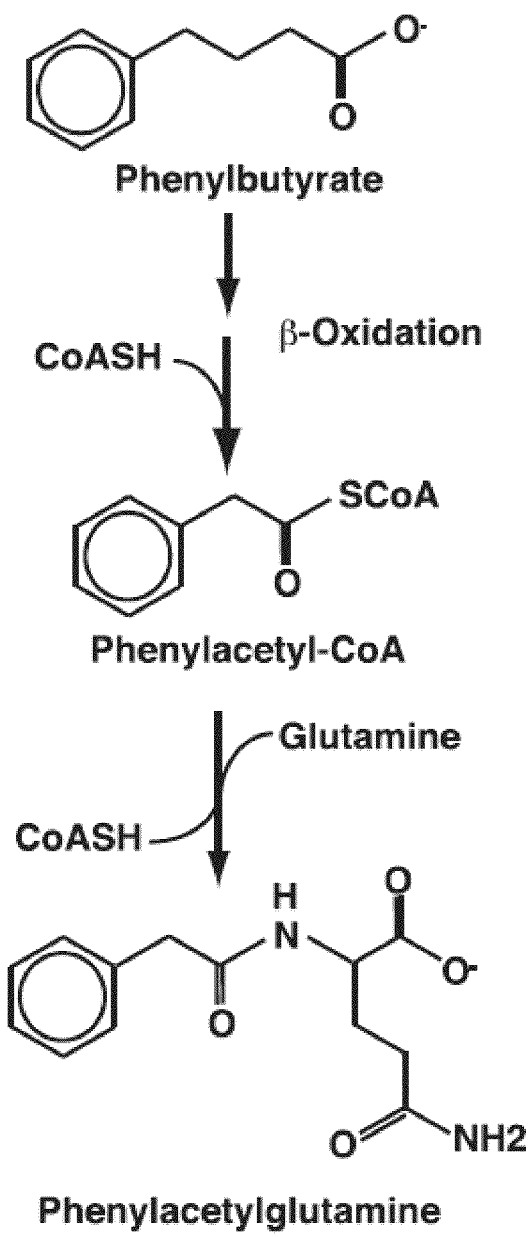

International Search Report dated Aug. 29, 2013 in PCT/US2013/036739.

Izai, et al., "Novel Fatty Acid β-Oxidation Enzymes in Rat Liver Mitochondria. 1. Purification and Properties of very-long-chain Acyl-Coenzyme A Dehydrogenase" J Biol Chem 267:1027-1033, 1992.

Kim, et al., "Crystal structures of medium-chain acyl-CoA dehydrogenase from pig liver mitochondria with and without substrate" Proc Natl Acad Sci USA 90:7523-7527, 1993.

Kormanik, et al., "Evidence for involvement of medium chain acyl-CoA dehydrogenase in the metabolism of phenylbutyrate", Molecular Genetics and Metabolism, Oct. 18, 2012 (E-pub.), vol. 107, pp. 684-689. See pp. 684-688.

Leys, et al., "Extensive conformational sampling in a ternary electron transfer complex" Nat Struct Biol 10:219-25, 2003.

Macheroux, et al., "Medium-Chain Acyl CoA Dehydrogenase: Evidence for Phosphorylation" Biol Chem. 378:1381-1385, 1997.

Matsubara, et al., "Molecular Cloning and Nucleotide Sequence of cDNAs Encoding the Precursors of Rat Long Chain Acyl-Coenzyme A, Short Chain Acyl-Coenzyme A, and Isovaleryl-Coenzyme A Dehydrogenases. Sequence Homology of Four Enzymes of the Acyl-CoA Dehydrogenase Family" J Biol Chem 264:16321-16331, 1989.

McKean, et al. "General Acyl-CoA Dehydrogenase from Pig Liver. Kinetic and binding studies" J Biol Chem 254:2730-2735, 1979.

Medicis Pharmaceutical Corporation. (2005-2006) 3Ucyclyd Pharma. "Buphenyl (sodium phenylbutyrate) Tablets and Powder" http://ureacycle.com/about-ucd.aspx.

Mohsen, et al., "High-level expression of an altered cDNA encoding human isovaleryl-CoA dehydrogenase in *Escherichia coli*" Gene 160: 263-267, 1995.

Mohsen, A.-W. and Vockley, J. in (Ghisla, S., Kroneck, P., Macheroux, P. and Sund, H., eds.) Flavins and Flavoproteins 1999, Rudolf Weber, New York 1999, pp. 515-518.

Nasser, et al., "Thermal unfolding of medium-chain acyl-CoA dehydrogenase and iso (3) valeryl-CoA dehydrogenase: study of the effect of genetic defects on enzyme stability" Biochim. Biophys. Acta 1690:22-32, 2004.

National Urea Cycle Disorders Foundation. (2005). http://www.nucdf.org/ucd_kinds.htm.

Nguyen, et al., "Identification of isobutyryl-CoA dehydrogenase and its deficiency in humans" Mol Genet Metab 77:68-79, 2002.

Ozand, P. T., "Hypoglycemia in association with various organic and amino acid disorders", Seminars in Perinatology, 2000, vol. 24, No. 2, pp. 172-193. See pp. 175-181 and 185.

Qi, et al., "Sodium 4-phenylbutyrate protects against cerebral ischemic injury" Mol Pharmacol 66:899-908, 2004.

Rozen, et al., "Isolation and Expression of a cDNA Encoding the Precursor for a Novel Member (ACADSB) of the Acyl-CoA Dehydrogenase Gene Family" Genomics 24:280-287, 1994.

Saito, et al., "Chromatin remodeling at Alu repeats by epigenetic treatment activates silenced microRNA-512-5p with downregulation of Mcl-1 in human gastric cancer cells" Oncogne 28:2738-2744, 2009.

Schimanski, et al., "A Novel Two-Nucleotide Deletion in the Ornithine Transcarbamylase Gene Causing Fatal Hyperammonia in Early Pregnancy", Hepatology, 1996, vol. 24, pp. 1413-1415.

Schulz, "Long Chain Enoyl Coenzyme A Hydratase from Pig Heart" J Biol Chem 249:2704-2709, 1974.

Thorpe, et al., "Acyl-Coenzyme A Dehydrogenase from Pig Kidney. Purification and Properties" Biochemistry 18: 331-337, 1979.

Thorpe, et al., "Structure and mechanism of action of the Acyl-CoA dehydrogenases" FASEB 9: 718-725, 1995.

Thorpe, et al., "The acyl-CoA dehydrogenases: Some mechanistic aspects" University of Calgary Press, Calgary, Canada, 1997, pp. 597-604.

Thorpe, et al., Electron-transferring flavoproteins In: Chemistry and Biochemistry of Flavoenzymes. CRC Press, Inc., Boca Raton, FL, 1991, pp. 471-486.

Toogood, et al., "Extensive Domain Motion and Electron Transfer in the Human Electron Transferring Flavoprotein Medium Chain Acyl-CoA Dehydrogenase Complex" J. Biol. Chem. 279: 32904-12, 2004.

Toogood, et al., "Stabilization of Non-productive Conformations Underpins Rapid Electron Transfer to Electron-transferring Flavoprotein" J. Biol. Chem. 280: 30361-30366, 2005.

Vilatoba, et al., "Sodium 4-phenylbutyrate protects against liver ischemia reperfusion injury by inhibition of endoplasmic reticulum-stress mediated apoptosis" Surgery 138:342-351, 2005.

Vockley, et al., "Mammalian branched-chain Acyl-CoA Dehydrogenases: Molecular cloning and characterization of the recombinant enzymes" Methods Enzymol 324:241-258, 2000.

Willard, et al., "Cloning of a cDNA for Short/Branched Chain Acyl-Coenzyme A Dehydrogenase from Rat and Characterization of its Tissue Expression and Substrate Specificity" Arch Biochem Biophys 331:127- 133, 1996.

Zhang, et al., "Cloning and functional characterization of ACAD-9, a novel member of human acyl-CoA dehydrogenase family" Biochem Biophys Res Commun 297:1033-1042, 2002.

Zhang, et al., "Structural Organization and Regulatory Regions of the Human Medium-Chain Acyl-CoA Dehydrogenase Gene" Biochemistry 31:81-9, 1992.

"Program for SIMD annual meeting", Molecular Genetics and Metabolism, vol. 105, No. 3, Mar. 1, 2012, pp. 273-366, XP055202401.

Kasumov, T., "New Secondary Metabolites of Phenylbutyrate in Humans and Rats", Drug Metabolism and Disposition, vol. 32, No. 1, Jan. 1, 2004, pp. 10-19, XP055019599.

EP Extended Search Report dated Oct. 29, 2015 in EP Application No. 13778033.4.

\* cited by examiner

TREATMENT OF MEDIUM-CHAIN ACYL-COA DEHYDROGENASE DEFICIENCY

CROSS-REFERENCE TO RELATED APPLICATION

This application is a continuation of International Patent Application PCT/US2013/036739, filed Apr. 16, 2013, and claims priority to U.S. Provisional Application Ser. No. 61/624,864 filed Apr. 16, 2012, to both of which priority is claimed and the contents of which are incorporated herein in their entireties.

STATEMENT REGARDING FEDERALLY SPONSORED RESEARCH OR DEVELOPMENT

This invention was made with government support under grant Number HD056004 awarded by the National Institutes of Health. The government has certain rights in the invention.

1. INTRODUCTION

The present invention provides for methods and compositions in which phenylbutyrate or other source of phenylacetate is used to treat medium-chain acyl CoA dehydrogenase deficiency.

2. BACKGROUND OF THE INVENTION

2.1 MCADD

Medium chain acyl-CoA dehydrogenase (MCAD) deficiency (MCADD) is an inborn error of fatty acid metabolism and rivals phenylalanine hydroxylase deficiency (PKU, Phenylketonuria) as the most common biochemical genetic disorder in the United States. The overall frequency of the disease has been estimated at 1:6,500 to 1:17,000 in Caucasians of mostly Northern European ancestry. The MCAD gene is located on chromosome 1p31 and contains 12 exons (Zhang et al., Biochemistry 31:81-9, 1992). An MCAD A985G point mutation has been identified in 90% of the alleles in the MCAD gene in deficient patients. This mutation substitutes a glutamate for a lysine at position 304 (K304E). Another common apparently silent mutation, A11610 (V362V) is found in some individuals in exon 11. Multiple mutations have been identified in the second allele 18 individuals having one A985G allele: G127A (E17K), T233C (I53T), 244 insertion T (D79X), G253T (G60C), T320C (L82S), A430T (K144X), 431-434 deletion AGTA (R123X), T464C (M130T), T499C (S142P), A589G (K172E), C631T (P186S), C683A (T203N), G799A (G242R), or G881C (R269T). All were found to be clinically affected. Heterozygotes are usually asymptomatic.

MCADD patients are asymptomatic at birth but are at risk for episodes of acute, life threatening metabolic decompensation. These usually first occur between 3 and 24 months of age but can occur at any age in association with physiologic stress such as fasting or infection, fever, or strenuous exercise. The mortality rate during an acute crisis in previously undiagnosed patients can be as high as 20%. MCADD can now be identified pre-symptomatically, nearly eliminating mortality due to this disease. However, there is currently no drug used to treat MCADD, and the standard of care requires lifelong dietary monitoring. Significant morbidity still occurs; for example, patients frequently require hospitalization for IV glucose therapy in the face of reduced oral intake during illnesses. Thus a medication capable of relieving the metabolic block would be of great benefit to these patients.

2.2 The Acyl-CoA Dehydrogenase Gene Family

MCAD is a member of the acyl-CoA dehydrogenase (ACD) family of enzymes, a group of structurally similar enzymes that catalyze the $\alpha,\beta$-dehydrogenation of acyl-CoA esters and transfer electrons to electron transferring flavoprotein (ETF). Biochemical and immunological studies have identified at least 9 distinct members of this enzyme family, each with a characteristic substrate specificity (Ikeda et al., J. Biol. Chem. 258: 1066-1076, 1983; Ikeda et al., J. Biol. Chem. 260: 1311-1325, 1985; Ikeda et al., J. Biol. Chem. 258: 9477-9487, 1983; Izai et al., J. Biol. Chem. 267:1027-1033, 1992; Rozen et al., Genomics 24: 280-287, 1994; Willard et al., Arch. Biochem. Biophys. 331:127-133, 1996; Nguyen et al., Mol. Genet. Metab. 77: 68-79, 2002; Zhang et al., Biochem. Biophys. Res. Commun. 297:1033-42, 2002). Very long, ACD9, long, medium and short chain acyl-CoA dehydrogenases (VLCAD, ACD9, LCAD, MCAD, and SCAD) catalyze the first step in the $\beta$-oxidation cycle with substrate optima of 16, 16:1, 14, 8 and 4 carbon chains respectively. Isovaleryl-CoA dehydrogenase (IVD), short/branched chain ACD (SBCAD), and isobutyryl-CoA dehydrogenase (IBD) catalyze the third step in leucine, isoleucine and valine metabolism, respectively (Ikeda et al., J. Biol. Chem. 258: 9477-9487, 1983; Rozen et al., Genomics 24: 280-287, 1994; Nguyen et al., Mol. Genet. Metab. 77: 68-79, 2002; Ikeda et al., J. Biol. Chem. 258: 1077-1085, 1983; Ikeda et al., Methods Enzymol 166: 360-73, 1988; Ikeda et al., Methods Enzymol 166: 374-89, 1988; Finocchiaro et al., J. Biol. Chem. 262: 7982-9, 1987; Binzak et al., Biochimica et Biophysica Acta 1382: 137-142, 1998), while glutaryl-CoA dehydrogenase (GDH) functions in the lysine catabolic pathway. While mature VLCAD and ACD9 are dimers, the other ACDs are homotetramers, with each monomer containing a non-covalently bound flavin adenine dinucleotide molecule (FAD) as a prosthetic group (Ikeda et al., J. Biol. Chem. 258: 1066-1076, 1983; Ikeda et al., Biochemistry 24: 7192-7199, 1985; Ikeda et al., J, Biol. Chem. 260: 1326-1337, 1985). All of these enzymes have been purified to homogeneity from tissue or recombinant sources, and antisera have been produced (Ikeda et al., J. Biol. Chem. 260: 1311-1325, 1985; Ikeda et al., J. Biol. Chem. 258: 9477-9487, 1983; Izai et al., J. Biol. Chem. 267:1027-1033, 1992; Nguyen et al., Mol. Genet. Metab. 77: 68-79, 2002; Ikeda et al., J. Biol. Chem. 258: 1077-1085, 1983; Binzak et al., Biochimica et Biophysica Acta 1382: 137-142, 1998, Finocchiaro et al., J. Biol. Chem. 263: 15773-80, 1988; Aoyama et al., Journal of Clinical Investigation 95: 2465-2473, 1995; Mohsen et al., Gene 160: 263-267, 1995). All of the ACDs have been postulated to share a common ordered BiBi type kinetic mechanism (Ghisla et al., Biochemistry 23: 3154-3161, 1984; Thorpe et al., FASEB 9: 718-725, 1995; Thorpe et al., C, Schaller R A, Mohsen A-W and Vockley J: The acyl-CoA dehydrogenases: Some mechanistic aspects. University of Calgary Press, Calgary, Canada, 1997, pp. 597-604). Reduction of the enzyme via dehydrogenation of the substrate occurs when a glutamate residue acting as a catalytic base abstracts the $\alpha$-carbon proR hydrogen of substrate as a proton. The $\beta$-carbon proR hydrogen transfers as a hydride to N-5 of FAD and a stable intermediate, the charge transfer complex (CTC), is formed. Following establishment of the CTC, reoxidation of the enzyme occurs when ETF interacts with the enzyme to release the product.

In the proposed enzyme mechanism of all ACD reactions, the formation of a charge-transfer complex is postulated to be initiated with the abstraction of the substrate pro-R α-hydrogen as a proton by an active site glutamate base. The pro-R β-hydrogen of the acyl moiety of the substrate is then transferred as a hydride to the N-5 of the flavin ring (Ikeda et al., J. Biol. Chem. 260: 1311-1325, 1985; Ikeda et al., Biochemistry 24: 7192-7199, 1985). In the absence of an electron acceptor, ETF, the transfer of the substrate pro-R β-hydrogen as a hydride to the N-5 of the FAD is postulated to be incomplete, creating a resonant donor/acceptor hybrid species, or the "charge-transfer complex", with the acyl-CoA substrate/product remaining tightly bound to the enzyme (Ikeda et al., J. Biol. Chem. 260: 1311-1325, 1985; Ikeda et al., Biochemistry 24: 7192-7199, 1985). The abstraction of the pro-R β-proton and a transfer of the pro-R β-hydride to form the charge-transfer complex has also been postulated to occur in a concerted fashion (Thorpe et al., FASEB 9: 718-725, 1995; Thorpe et al., C: Electron-transferring flavoproteins. In: Chemistry and Biochemistry of Flavoenzymes. CRC Press, Inc., Boca Raton, Fla., 1991, pp 471-486; Thorpe et al., Biochemistry 18: 331-337, 1979). This interaction between the substrate, the active site base, and the oxidized FAD disrupts the extended π-electron system of the FAD isoalloxazine ring, quenching its characteristic absorbency at 445-450 nm and causing a new absorption band to appear at 580 nm. Under physiological conditions, the charge-transfer complex interacts with ETF, and the reduced ETF and enoyl-CoA are released as the end products to regenerate the oxidized enzyme (Ikeda et al., Biochemistry 24: 7192-7199, 1985; Ikeda et al., J. Biol. Chem. 260: 1326-1337, 1985; Thorpe et al., FASEB 9: 718-725, 1995; Thorpe et al., C, Schaller R A, Mohsen A-W and Vockley J: The acyl-CoA dehydrogenases: Some mechanistic aspects. University of Calgary Press, Calgary, Canada, 1997, pp. 597-604; Massey V: A simple method for the determination of redox potentials. In: Yagi K (ed) Flavins and Flavoproteins 1990, Walter deGruyte, New York, 1991, pp 59-86). Important clues for deciphering the mechanism of interaction between ETF and its redox partners have been obtained with the crystallization of human MCAD:ETF (PDB: 2A1T) and *M. methylotrophus* trimethylamine dehydrogenase:ETF (PDB: 1UDY) ternary complexes (Leys et al., Nat Struct Biol 10:219-25, 2003; Toogood et al., J. Biol. Chem. 279: 32904-12, 2004; Toogood et al., J. Biol. Chem. 280: 30361-30366, 2005). The crystallization of ETF with these two different redox partners suggests that ETF could bind to its partner without the former necessarily being reduced or being in the binary complex form with substrate. They also show that the identity of the recognition/anchor site of ETF for its binding partners is the same for the different enzymes. Another important feature that these two complexes share is that the β-subunit containing the recognition-anchor domain acts to provide a static binding force, while domain II, which is responsible for electron transfer, is so highly dynamic that it is absent from the electron density data collected.

2.3 Sodium Phenylbutyrate

Sodium phenylbutyrate ("Buphenyl®") is a commercially available drug used for treating PKU, where phenylbutyrate removes excess ammonia by conjugating its active form, phenylacetate, with glutamine. Buphenyl® is converted into this active form after one cycle of β-oxidation.

3. SUMMARY OF THE INVENTION

The present invention provides for methods and compositions for treating MCADD. It is based, at least in part, on the discovery that phenylbutyrate can serve as a substrate for MCAD. In non-limiting embodiments, phenylbutyrate or another source of phenylacetate is administered as a chaperone treatment to patients suffering from MCADD. The present application also provides for compositions comprising phenylbutyrate or another source of phenylacetate, for use in the preparation of a medicament for treating MCADD.

4. BRIEF DESCRIPTION OF THE FIGURES

FIG. 1: Schematic showing a proposed overall pathway for metabolism of phenylbutyrate to its final metabolite.

Figure 2:
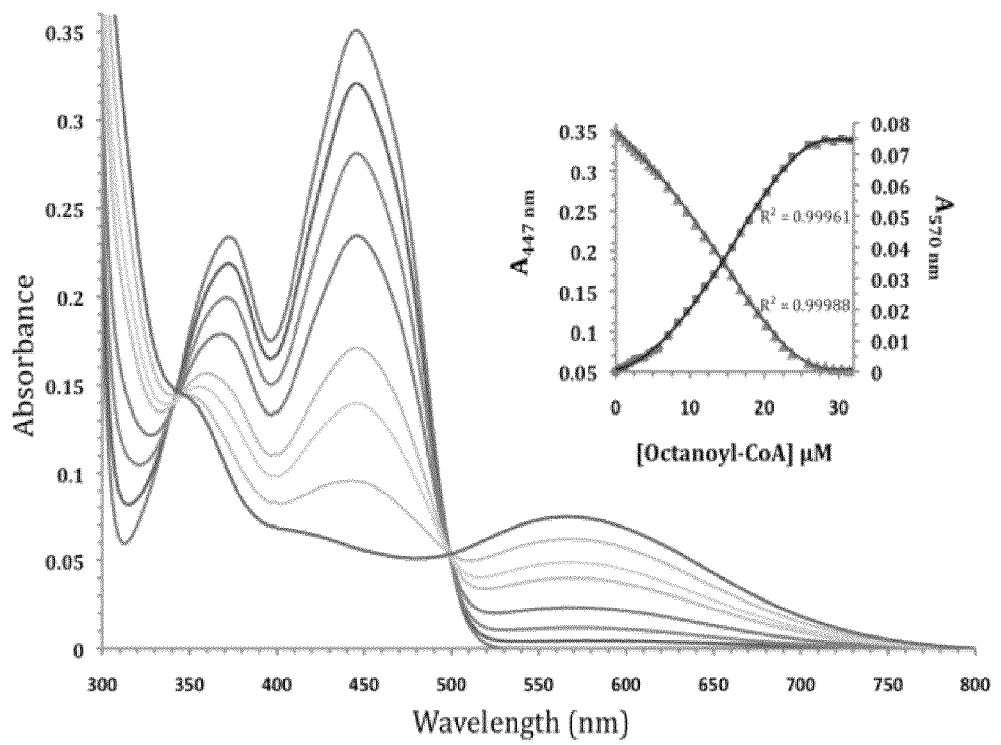

FIG. 2: Monitoring the formation of the charge transfer complex with purified MCAD upon addition of increasing amounts of octanoyl-CoA. The absorbance maxima at ~370 nm and ~447 nm are reduced and a new peak centered at ~570 nm appears with addition of increasing substrate. Selected scans are shown with octanoyl-CoA concentration at 0, 3.25, 7.1, 10.8, 15.6, 18.0, 21.5, and 28.2 µM. The inset shows the kinetics of these changes. Enzyme concentration was 25.2 µM. Equation for the decrease at 447 nm is: $y=-1\times10^{-9}x^6+1\times10^{-7}x^5-2\times10^{-6}x^4+2\times10^{-5}x^3-0.0003x^2-0.008x+0.3489$. Equation for the increase at 570 nm is: $y=6\times10^{-10}x^6-5\times10^{-8}x^5+1\times10^{-6}x^4-2\times10^{-5}x^3+0.0003x^2+0.0003x+0.0008$.

Figure 3:
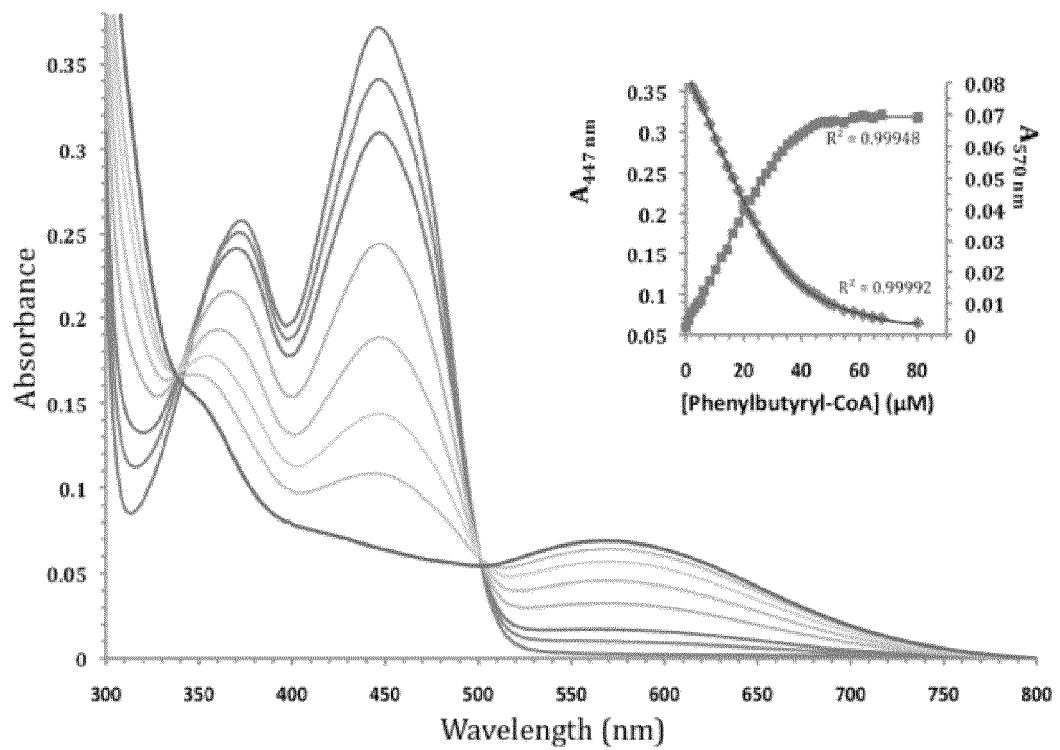

FIG. 3: Monitoring the formation of the charge transfer complex with purified MCAD upon addition of increasing amounts of phenylbutyryl-CoA. The absorbance maxima at ~370 nm and ~447 nm are reduced and a new peak centered at ~570 nm appears with addition of increasing substrate. Selected scans are shown with phenylbutyryl-CoA concentration at 0, 4.2, 8.3, 16.3, 24.1, 31.6, 40.7, and 80.2 µM. The inset shows the kinetics of these changes. Enzyme concentration was 25.2 µM. Equation for the decrease at 447 nm is: $y=5\times10^{-10}x^5-1\times10^{-7}x^4+9\times10^{-6}x^3-0.0002\ x^2-0.0061\ x+0.3707$. Equation for the increase at 570 nm is: $y=-1\times10^{-10}x^5+3\times10^{-8}x^4-3\times10^{-6}x^3+7\times10^{-5}x^2+0.0012\ x+0.0036$.

Figure 4:
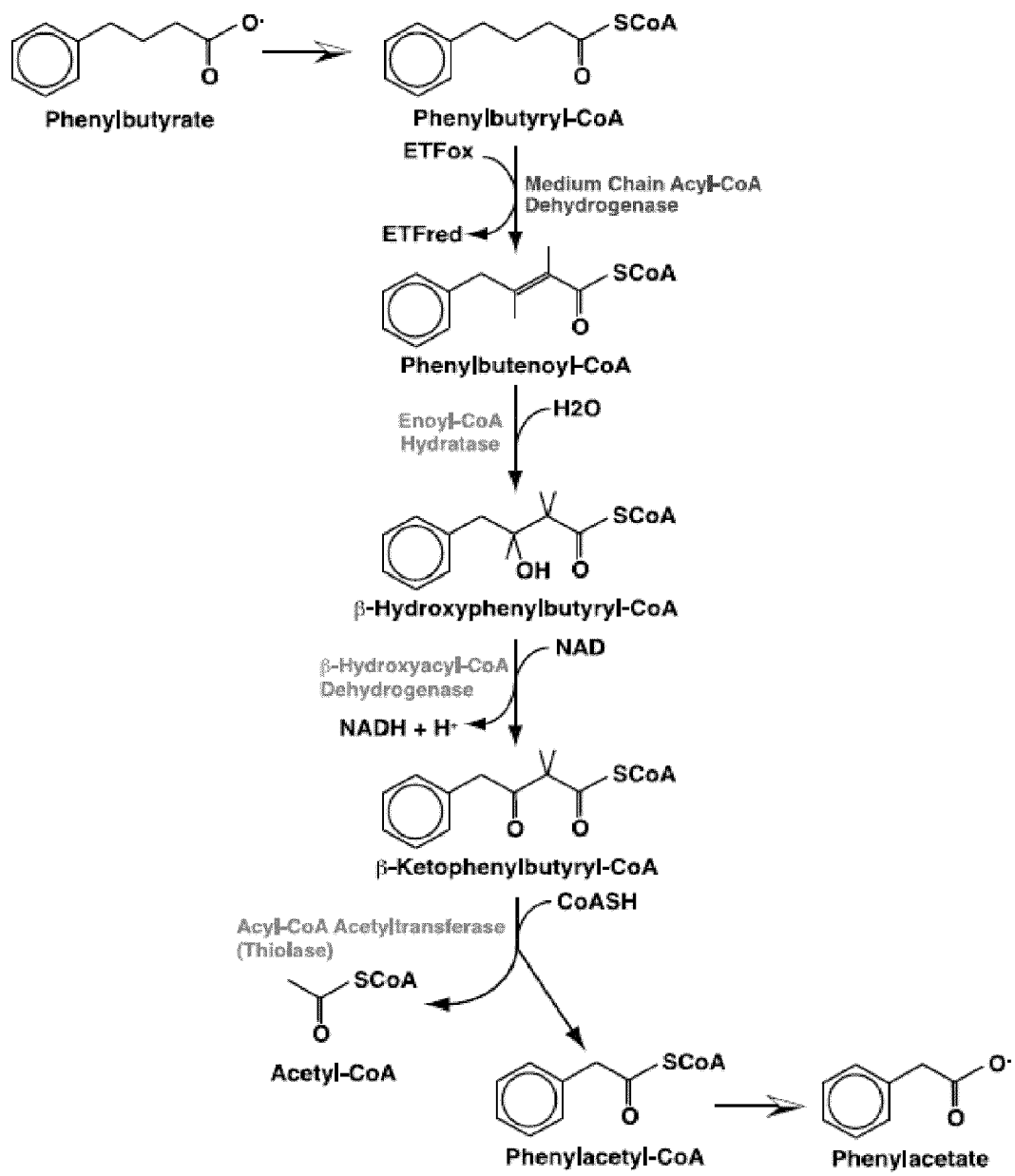

FIG. 4: Detailed proposed pathway of metabolism of phenylbutyrate to its active form, phenylacetate.

Figure 5:
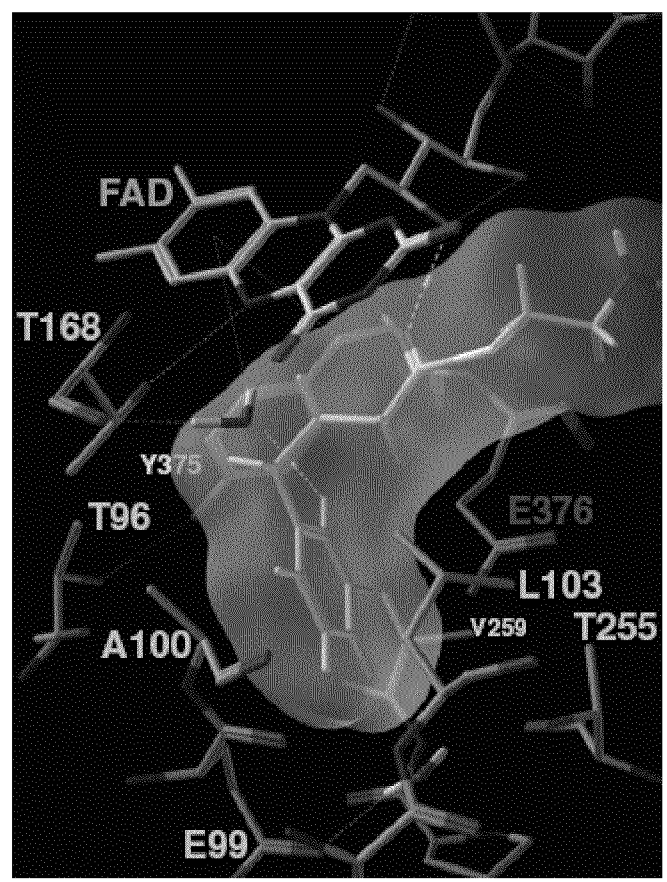

FIG. 5: Stick representation of MCAD active site residues and ligands with phenylbutyryl-CoA modeled in place of octanoyl-CoA. The crystal structure of pig MCAD with bound octanoyl-CoA (PDB: 3MDE, (23)) was used to create the model using MOE modeling software. The E376 carboxylate is the active site catalytic base responsible for the substrate C2 proton abstraction to initiate catalysis.

5. DETAILED DESCRIPTION OF THE INVENTION

The present invention relates to methods and compositions for treating subjects with MCADD with phenylbutyrate and/or another source of phenylacetate.

A subject may be a human or non-human subject such as a dog, cat, horse, pig, cow, sheep, goat, rodent, rabbit, etc.

In certain non-limiting embodiments, phenylbutyrate is administered as a salt, for example, but not limited to, sodium phenylbutyrate. In a specific, non-limiting embodiment, Buphenyl® is used.

In certain non-limiting embodiments, the source of phenylacetate is a composition comprising phenylacetate. For example, in one specific non-limiting embodiment, the composition is a mixture of sodium benzoate and sodium phenylacetate (e.g. Ammonul®), which may be administered intravenously (for example, to subjects for which oral administration would be problematic).

In another specific non-limiting embodiment, a prodrug of phenylbutyrate and/or of phenylacetate, for example triphenylbutyrylglycerol (also known as glycerol phenylbutyrate, benzenebutanoic acid, 1',1"-(1,2,3-propanetriyl) ester and RAVICTI™), AN-113 (also known as butyroyloxymethyl-4-phenylbutyrate), or combinations thereof, is used.

Phenylbutyrate, for example as a salt, may be administered by a route selected from the group consisting of oral, intravenous, intrathecal, intraperitoneal, nasal, pulmonary, rectal, vaginal, subcutaneous, intradermal, or intramuscular. It may be administered via a reservoir.

In certain, non-limiting embodiments, the present invention provides for a method of treating a subject with MCADD comprising administering, to the subject, an effective amount of phenylbutyrate, for example as a phenylbutyrate salt, as a regular therapy regimen. In a regular therapy regimen, phenylbutyrate is administered on a regular basis, for example, but not limited to: each time the subject eats, with each meal, once a day, twice a day, three times a day, four times a day, five times a day, six times a day, every 24 hours, every 12 hours, every eight hours, every six hours, or every four hours. The regular therapy regimen may be administered for a duration that may be, for example, but not limited to: continuous (without a planned termination), one year, one month, two months, three months, four months, five months, six months, seven months, eight months, nine months, ten months, eleven months, one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks; twenty weeks; twenty eight weeks, one day, two days, three days, four days, five days, six days, seven days, eight days, nine days, ten days, eleven days, twelve days, thirteen days, fourteen days, fifteen days, sixteen days, seventeen days, eighteen days, nineteen days, twenty days, twenty-one days, twenty-two days, twenty-three days, twenty-four days, twenty-five days, twenty-six days, twenty-seven days, twenty-eight days, twenty-nine days, thirty days, or thirty-one days.

In certain, non-limiting embodiments, the present invention provides for a method of treating a subject with MCADD comprising administering, to the subject, an effective amount of phenylbutyrate, for example as a phenylbutyrate salt, when the subject is at metabolic risk. The subject is at metabolic risk as a result of one or more of the following: infection; a planned or passed interval without food ("a fasting interval") of at least six hours, or at least about 8 hours, or at least about 10 hours, or at least about 12 hours, or at least about 18 hours, or at least about 24 hours; and/or an intercurrent illness leading to increased metabolic energy demand and/or reduction of food intake. The phenylbutyrate, for example as a phenylbutyrate salt, may be administered, for example, but not by limitation: each time the subject eats, with each meal, once a day, twice a day, three times a day, four times a day, five times a day, six times a day, every 24 hours, every 12 hours, every eight hours, every six hours, every four hours, every two hours, or every hour. In specific non-limiting embodiments, the treatment interval may be: for the duration of the period over which the subject is at metabolic risk; for one day, two days, three days, four days, five days, six days, seven days, eight days, nine days, ten days, eleven days, twelve days, thirteen days, fourteen days, fifteen days, sixteen days, seventeen days, eighteen days, nineteen days, twenty days, twenty-one days, twenty-two days, twenty-three days, twenty-four days, twenty-five days, twenty-six days, twenty-seven days, twenty-eight days, twenty-nine days, thirty days, or thirty-one days.

In certain non-limiting embodiments, the phenylbutyrate may be administered as sodium phenylbutyrate (e.g., Buphenyl®). In specific non-limiting embodiments, sodium phenylbutyrate may be administered orally. The maximum daily dose of sodium phenylbutyrate is 20 grams per day. In specific non-limiting embodiments, sodium phenylbutyrate may be administered at a dosage of 450-600 mg/kg/day in subjects weighing less than 20 kg. In specific non-limiting embodiments, sodium phenylbutyrate may be administered at a dosage of 9.9-13.0 g/m²/day for subjects weighing 20 kg or more. In a specific, non-limiting embodiment, the daily dose of sodium phenylbutyrate may be divided into 4, 5, or 6 dosages. In specific non-limiting embodiments, sodium phenylbutyrate may be administered at a dose of less than 450 mg/kg/day. In specific non-limiting embodiments, sodium phenylbutyrate may be administered at a dose of between 200-400 mg/kg/day. In specific non-limiting embodiments, sodium phenylbutyrate may be administered at a dose of 4-8 g/m²/day. In specific non-limiting embodiments, sodium phenylbutyrate may be administered at a dose of 4-6 g/m²/day. In specific non-limiting embodiments, sodium phenylbutyrate may be administered at a dosage of 0.5 g. In specific non-limiting embodiments, sodium phenylbutyrate may be administered at a dosage of 1 g. In specific non-limiting embodiments, sodium phenylbutyrate may be administered at a dosage of 2 g.

In certain non-limiting embodiments, a prodrug of phenylbutyrate and/or of phenylacetate, for example, triphenylbutyrylglycerol (i.e., RAVICTI™), AN-113, or combinations thereof, is administered according to the present application. In specific non-limiting embodiments, the prodrug may be administered orally. In certain non-limiting embodiments, the maximum daily dose of RAVICTI™ is 17.5 mL, or 19 grams per day. In specific non-limiting embodiments, RAVICTI™ may be administered at a dosage of 4.5-11.2 mL/m²/day. In specific non-limiting embodiments, RAVICTI™ may be administered at a dosage of about 5-12.4 g/m²/day. In a specific, non-limiting embodiment, the daily dose of RAVICTI™ may be divided into 2, 3, 4, 5, or 6 dosages. In certain non-limiting embodiments, the RAVICTI™ is administered to a patient who is naïve to phenylbutyrate. In certain non-limiting embodiments, RAVICTI™ is administered to a patient who has previously been treated with sodium phenylbutyrate, wherein the prodrug is administered in an amount equal to 0.86 times the total daily dosage of phenylbutyrate previously administered to treat the patient.

In specific non-limiting embodiments, RAVICTI™ may be administered at a dose of less than 19 g/day. In specific non-limiting embodiments, RAVICTI™ may be administered at a dose of between 0.5-4.0 mL/m²/day. In specific non-limiting embodiments, RAVICTI™ may be administered at a dose of between 0.1-0.5 mL/m²/day. In specific non-limiting embodiments, RAVICTI™ may be administered at a dose of 0.5-4 g/m²/day. In specific non-limiting embodiments, RAVICTI™ may be administered at a dose of 0.1-0.5 g/m²/day. In specific non-limiting embodiments, RAVICTI™ may be administered at a dosage of 0.5 g/m²/day. In specific non-limiting embodiments, RAVICTI™ may be administered at a dosage of 1 g/m²/day. In specific non-limiting embodiments, RAVICTI™ may be administered at a dosage of 2 g/m²/day. In specific non-limiting embodiments, RAVICTI™ may be administered at a dosage of 5 g/m²/day. In specific non-limiting embodiments, RAVICTI™ may be administered at a dosage of 10 g/m²/day. In specific non-limiting embodiments, RAVICTI™ may be administered at a dosage of 0.5 mL/m²/day. In specific non-limiting embodiments, RAVICTI™ may be administered at a dosage of 0.6 mL/m²/day. In specific non-limiting embodiments, RAVICTI™ may be administered at a dosage of 1 mL/m²/day. In specific non-limiting embodiments, RAVICTI™ may be administered at a dosage of 2 mL/m²/day. In specific non-limiting embodiments, RAVICTI™ may be administered at a dosage of 4 mL/m²/day. In specific non-limiting embodiments, RAVICTI™ may be administered at a dosage of 4.5 mL/m²/day. In specific non-limiting embodiments, RAVICTI™ may be administered at a dosage of 5 mL/m²/day. In specific non-limiting embodiments, RAVICTI™ may be administered at a dosage of 10 mL/m²/day.

In certain non-limiting embodiments, a prodrug is administered at a dosage of about 10 to about 50 fold lower than an effective dosage of phenylbutyrate. In certain non-limiting embodiments, a prodrug is administered at a dosage of about 15 to about 25 fold lower than an effective dosage of phenylbutyrate. In certain non-limiting embodiments, a prodrug is administered at a dosage of about 20 fold lower than an effective dosage of phenylbutyrate.

In certain non-limiting embodiments, a mixture of sodium phenylacetate and sodium benzoate may be administered to the subject, for example, but not limited to, Ammonul®. In a specific, non-limiting embodiment, for subjects weighing less than 20 kg, 0.25 g/kg of each of sodium benzoate and sodium phenylacetate may be administered daily, or, if the subject weighs more than 20 kg, 5.5 g/m² of each of sodium benzoate and sodium phenylacetate may be administered daily.

6. EXAMPLE

Medium Chain Acyl-CoA Dehydrogenase Plays a Key Role in Metabolism of Phenylbutyrate

6.1 Materials and Methods

Purification of Recombinant Human MCAD.

Expression and purification of recombinant human MCAD was perforated as previously described for isovaleryl-CoA dehydrogenase with minor modifications (18). *E. coli* JM105 cells (Amersham Biosciences Corp; Piscataway, N.J.) containing the human MCAD high expression vector pKeMCAD (19) and a GroEL/GroES expression plasmid were grown overnight in a 200-ml LB broth pre-culture that was used to inoculate 4×2-L cultures in 2-YT broth. The cells were left to grow overnight at 37° C. with shaking and MCAD expression was induced the next morning using IPTG at a final concentration of 0.5 mM for 3 hrs. Cells were harvested by centrifugation and resuspended at 4° C. in 2:1 weight to volume of 100 mM potassium phosphate pH 8.0, 150 mM EDTA. Cells were then lysed by sonication on ice. Including high amounts of EDTA in the cell lysis buffer can protect residues with groups, e.g., cysteine thiols and methionine sulfide groups, vulnerable to modification by oxygen reactive species generated during sonication cell suspension. This was effective in improving enzyme preparations resulting higher specific activity and consistent kinetic behavior. Cellular debris was removed by centrifugation first at 250,000×g for 60 minutes each. The final supernatant was dialyzed for 4 hours with vigorous stirring in 50 mM potassium phosphate pH 8.0, at 4° C. The sample was then loaded on a 16×40 mm DEAE Sepharose FF column pre-equilibrated in 50 mM potassium phosphate pH 8.0, using an ÄKTA UPC-900 pump FPLC system (Amersham Biosciences Corp; Piscataway, N.J.). After washing with 300 ml of 50 mM potassium phosphate pH 8.0, MCAD was eluted with a 300 ml linear gradient from 50 to 500 mM potassium phosphate pH 8.0. Green fractions with a 270/447 nm ratio<12 containing MCAD were pooled, concentrated, and dialyzed against 25 mM potassium phosphate, pH 8.0. Pooled fractions of essentially pure MCAD (270/447 nm ratio=5.5), were concentrated and stored at −80° C. Other recombinant human ACADs were similarly purified except that the protocol was terminated after the DEAE-Sepharose column for human recombinant LCAD as the enzyme was unstable. LCAD protein purity was at about 70% at this stage.

ETF Purification.

Porcine ETF was purified as previously published (20), except that the dialysis buffer used after both the 40-60% ammonium sulfate fractionation and DE-52 cellulose anion-exchange chromatography steps consisted of unbuffered 15 mM dibasic potassium phosphate and 5% glycerol.

Fibroblast Cell Culture and Extract Preparation.

Wild type and MCAD deficient cells (homozygous for the K304E mutation) with the designation GM085401 and GM07844, respectively, were obtained form Coriell Institute for Medical Research, Camden, N.J. Cells were cultured in DMEM medium supplemented with glutamine and ampicillin and streptomycin, and 20% fetal bovine serum. Cells were harvested from a T175 flask by sonication with a buffer consisting of 50 mM Tris buffer and 10 mM EDTA, pH 8.0. The cell debris was removed by centrifugation and the cell free extract was assayed for protein and enzyme activity as described below.

ETF Fluorescence Reduction Assay.

The ETF reduction assay was performed using a Jasco FP-6300 spectrofluorometer (Easton, Md.) with a cuvette holder heated with circulating water at 32° C. The assay was otherwise performed as described (22), at the indicated substrate concentrations. The enzyme was diluted 1200-fold into a buffer containing 50 mM Tris, pH 8.0, 5 mM EDTA and 50% glycerol, and 10 μl were used for each assay. The ETF concentration in the reaction mixture was 2 μM. Spectra Manager 2 software (Jasco Inc) was used to collect data and calculate reaction rate and Microsoft Excel was used to calculate the kinetic parameters.

Phenylbutyryl-CoA Synthesis.

CoASH, octanoyl-CoA, C12-CoA and phenylbutyric acid were obtained from Sigma (St. Louis, Mo.) 2,6-dimethylheptanoic acid was obtained from Matreya LLC (Pleasant Gap, Pa.). The phenylbutyryl-CoA and 2,6-dimethylheptanoyl-CoA esters were prepared by the mixed anhydride method as described previously (24) and was purified by HPLC using a Luna 5 μm C18(2) column (25 cm×0.46 cm) and a linear gradient (10-60%) of acetonitrile into 50 mM ammonium phosphate, pH 5.5, at a flow rate of 1.5 mL/min over 30 min.

Monitoring the Interaction of MCAD with Substrates.

Formation of the charge transfer ternary complex was monitored by observing the increase in absorbance at the 570 nm area, concomitant with the decrease of absorbance at 447 nm area, of the purified MCAD in 120 mM potassium phosphate spectrum under anaerobic conditions using a Jasco V-650 Spectrophotometer. A quartz cuvette with a round top containing 0.5 ml of the purified MCAD in 120 mM potassium phosphate, pH 8.0, was sealed with a rubber plug, and using a needle, ten alternating cycles of vacuum and argon were applied to remove oxygen. One μL at a time of phenylbutyryl-CoA solution dissolved in water to 0.53 mM was then added to the sample in the sealed cuvette using a 50 μl Hamilton syringe attached to an automatic dispenser. Ten seconds of equilibration time were allowed after mixing and the sample was scanned for UV/Visible light absorbance at 250 to 800 nm. Final substrate concentrations varied from 0 to 28.2 μM for octanoyl-CoA and 0 to 80.2 μM for phenylbutyryl- CoA. All data were adjusted for the dilution resulting from substrate addition. Substrates were titrated, but with different final concentrations as indicated in the figure legends. The "apparent" productive-binding constant (Kd app) was calculated with the following equation:

$$\frac{d}{p} = K_{D\,app} \frac{1}{e-p} + n$$

where d is the total ligand concentration, e is the total molar concentration of enzyme, p is the fraction of enzyme sites that bind ligand multiplied by e, and n is the number of binding sites. The absorbance at 447 nm when all enzyme sites are occupied with ligand was determined separately by adding large excess of octanoyl-CoA and used to calculate the fraction of enzyme with bound ligand at various readings and assuming that at large excess of added substrate would equal to e.

Molecular Modeling.

Computer modeling of MCAD was performed using a Silicon Graphics Fuel workstation (Mountain View, Calif.) with the Insight II 2005 software package and MOE software, from Chemical Computing Group, Montreal, Canada, and the atomic coordinates of pig MCAD (3MDE) in the dimer form as a molecule (23). Carbon atoms at positions C5-C8 of the octanoyl-CoA ligand, which co-crystallized with MCAD, were replaced with a phenyl group. The phenylbutyryl-CoA ligand conformation in the active site was refined using the Discover module. Human LCAD 3D structure was modeled using MCAD atomic coordinates as template and the Insight II modeling software.

6.2 Results

Interaction of MCAD with Substrates, the Reductive Half-Reaction. Formation of the charge transfer complex, the reductive half-reaction, is evident from the spectral scans of MCAD at various phenylbutyryl-CoA concentrations (FIGS. 2 and 3). The progressive decrease and increase of absorbance at 447 nm and 570 nm, respectively, are similar to those induced by octanoyl-CoA. The octanoyl-CoA binding curve is sigmoidal in contrast to the phenylbutyryl-CoA binding curve, possibly reflecting differences in enzyme mechanism of interaction. The plot of d/p versus 1/e–p (the Stockell plot) was nonlinear. A line drawn at the straight area of the curve where the substrate:subunit ratio was 1:1 estimates the apparent dissociation constant ($K_D$ app) being 0.12 µM and 2.16 µM for octanoyl-CoA and phenylbutyryl-CoA, respectively. Other mathematical derivatives of the absorbance data all indicated that the binding sites are non-equivalent.

Interaction of MCAD:Substrate Ternary Complex with ETF, the Oxidative Half-Reaction.

Transfer of electrons is evident from decrease in ETF fluorescence when ETF is used as the electron acceptor in the presence of various concentrations of phenylbutyryl-CoA. The catalytic efficiency and $K_m$ for the phenylbutyryl-CoA were 0.2 mM$^{-1}$sec$^{-1}$ and 5.3 µM compared to 4.0 mM$^{-1}$sec$^{-1}$ and 2.8 µM for octanoyl-CoA, respectively.

Molecular modeling of human LCAD shows possible accommodation of the acyl moiety of the phenylbutyryl-CoA, with the exception of residue L264, which would have one of its side chain methyl hydrogens ~1.3 Å away from a phenyl ring hydrogen and so would hinder binding. To test if the LCAD active site has enough plasticity to accommodate this potential substrate, we measured its activity with LCAD using the ETF fluorescence reduction assay. While the partially purified recombinant human LCAD was active in the presence of various substrates including $C_{12}$-CoA and 2,6-dimethylheptanoyl-CoA, it was not active in the presence of phenylbutyryl-CoA. Purified SCAD, MCAD, and ACAD9 also showed no activity with phenylbutyryl-CoA as substrate.

The ETF Fluorescence Reduction Assay of Cell Extract.

ETF fluorescence reduction was observed using extracts from wild type fibroblast cells in the presence of 30 µM of phenylbutyryl-CoA, octanoyl-CoA, or palmitoyl-CoA. (The latter substrate was used as internal control and is a substrate of VLCAD.) Enzyme specific activity measured using these substrates was 3.41 (±0.53), 4.01 (±1.34), 9.10 (±2.13) nmoles ETF reduced×min$^{-1}$×mg$^{-1}$, respectively. No activity was observed using similar amounts of extract from fibroblast cells deficient in MCAD with either phenylbutyryl-CoA or octanoyl-CoA. The measured enzyme specific activity of palmitoyl-CoA oxidation in extract from these cells was 3.91 (±1.34) nmoles ETF reduced×min$^{-1}$×mg$^{-1}$.

6.3 Discussion

Following the conversion of phenylbutyrate to the CoA ester, one cycle of β-oxidation is expected to result in phenylacetyl-CoA and acetyl-CoA as the final products. (FIG. 4). Phenylacetyl-CoA is hydrolyzed to phenylacetate, which becomes conjugated with glutamine and is excreted in urine (FIG. 1). An analysis of this first step in the β-oxidation of phenylbutyryl-CoA is important because the first step in the β-oxidation of fatty acids is postulated to be rate-limiting, and thus the metabolism of phenylbutyrate to its active form, phenylacetate, may also be modulated by similar factors that affects energy metabolism at the same step (25).

The effect of phenylbutyryl-CoA on the MCAD absorbance spectrum at relatively low concentrations is monitored via the decrease of absorbance at 447 nm and increase of absorbance at 570 nm. This confirms productive binding of phenylbutyryl-CoA to MCAD in the reductive half-reaction with lack of product release. This effect is similar to that induced by octanoyl-CoA binding to MCAD, and indicative of the transfer of a proton and a hydride to the flavin ring and formation of the charge transfer complex, which is comprised of the enzyme, reduced FAD, and enoyl product and detected by the intense absorbance band centered at 570 nm.

The inset in FIG. 2 shows, however, a sigmoidal shaped curve induced by addition of octanoyl-CoA, with an exponential change phase centering at subunit:substrate ratio of 4:1. This corresponds to one octanoyl-CoA molecule binding the first subunit. Such a behavior was not detected when phenylbutyryl-CoA was used as substrate. This may imply positive cooperativity between the first and second subunits when octanoyl-CoA, but not phenylbutyryl-CoA, is used as substrate. Although other interpretations of sigmoidal behavior in this setting are possible, including presence of various MCAD forms or other effector molecules, the argument is weakened by the fact that the only difference between the two reactions is the substrate itself. Impurities in the substrate preparation are also not likely to induce such an effect as such impurities would be present at ineffectively low concentrations at the low substrate concentrations range, between 0.25-1 and 4:1 substrate:MCAD tetramer ratio. Why this kinetic behavior has not been reported earlier is perhaps due to the method of isolation and purification of the MCAD protein. Our current standard protocol for recombinant protein purification includes adding high concentrations of EDTA in the cell lysis buffer to protect residues with groups, e.g., cysteine thiols and methionine sulfide groups, vulnerable to modification by oxygen reactive species generated when sonication is used to break the *E. coli* cell wall. Using EDTA to protect residues from oxygen radical species has proven to be effective in providing our enzyme preparations with higher specific activity and consistent kinetic behavior (26).

Reduction of ETF by the charge transfer complex in the oxidative half-reaction shows that electrons from the bound phenylbutyryl-CoA can be productively transferred to ETF and the product, phenylbutenoyl-CoA, is released to complete the reaction. In contrast, none of the other ACADs are capable of catalyzing this reaction.

Modeling of a phenylbutyryl moiety in the active site in place of the octanoyl moiety observed in the MCAD crystal structure shows the phenyl moiety accommodated in the acyl moiety binding site pocket with a conformation perpendicular to the aromatic ring of Y375, FIG. 5. Other residues involved in binding the phenyl moiety include E99, A100, Leu103, and V259. Furthermore, modeling predicts that the phenyl ring para and/or meta positions are candidate expansion sites for adding a functional group that may improve binding, while addition at the ortho position would prevent the derivative from binding to MCAD.

Based on the kinetic parameters of MCAD with phenylbutyryl-CoA as substrate, individuals with MCAD deficiency are likely to experience a functionally relevant decrease in the ability to metabolize the medication (e.g., phenylbutyrate), though indications for use in these patients are likely to be rare. Of note, since octanoyl-CoA has been reported to provide thermal stability to the MCAD K304E mutant [27], it is possible that phenylbutyryl-CoA would behave similarly and may be of benefit in vivo in patients carrying at least one copy of this mutation. It is unknown if carriers for MCAD deficiency, a much more common situation, will display altered metabolism of phenylbutyrate. In other indications where the functional effects of phenylbutyrate are less well characterized, modulation of MCAD activity might be of benefit to alter drug metabolism and/or its half-life and increase its efficacy, depending on the mechanism of action of the medication in each disorder.

REFERENCES (1) National Urea Cycle Disorders Foundation. (2005). http://www.nucdf.org/ucd_kinds.htm
(2) Medicis Pharmaceutical Corporation. (2005-2006) 3Ucyclyd Pharma. "BUPHENYL (sodium phenylbutyrate) Tablets and Powder" http://ureacycle.com/about-ucd.aspx.
(3) Gore S D, Weng L J, Zhai S, Figg W D, Donehower R C, Dover G J, Greyer M, Griffin C A, Grochow L B, Rowinsky E K, Zabalena Y, Hawkins A L, Burks K, Miller CB (2001). Impact of the putative differentiating agent sodium phenylbutyrate on myelodysplastic syndromes and acute myeloid leukemia. *Clinical Cancer Res* 8:2330-2339.
(4) Saito, Y., Suzuki, H., Tsugawa, H., Nakagawa, I., Matsuzaki, J., Kanai, Y., Hibi, T. (2009). Chromatin remodeling at Alu repeats by epigenetic treatment activates silenced microRNA-512-5p with downregulation of Mcl-1 in human gastric cancer cells. *Oncogne* 38:2738-2744.
(5) Egger, G., Aparicio, A. M., Escobar, S. G., Jones, P. A. (2007). Inhibition of histone deacetylation does not block resilencing of p16 after 5-aza-2'-deoxycytidine treatment. *Cancer Res* 67:346-353.
(6) Vilatoba, M., Eckstein, C., Bilbao, G., Smyth, C. A., Jenkins, S., Thompson, J. A., Eckhoff, D. E., Contreras, J. L. (2005) Sodium 4-phenylbutyrate protects against liver ischemic reperfusion injury by inhibition of endoplasmic reticulum-stress mediated apoptosis. *Surgery* 138:342-351.
(7) Qi, X., Hosoi, T., Okuma, Y., Kaneko, M., Nomura, Y. (2004). Sodium 4-phenylbutyrate protects against cerebral ischemic injury. *Mol Pharmacol* 66:899-908.
(8) Ikeda Y, Dabrowski C, Tanaka K. (1983). Separation and properties of five distinct acyl-CoA dehydrogenases from rat liver mitochondria. *J Biol Chem* 258:1066-1076.
(9) Ikeda Y, Okamura-Ikeda K, Tanaka K. (1985). Purification and characterization of short-chain, medium-chain, and long-chain acyl-CoA dehydrogenases from rat liver mitochondria. Isolation of the holo- and apoenzymes and conversion of the apoenzyme to the holoenzyme. *J Biol Chem* 260:1311-1325.
(10) Ikeda Y, Tanaka K. (1983). Purification and characterization of 2-methyl-branched Chain acyl Coenzyme A dehydrogenase, an enzyme involved in isoleucine and valine metabolism, from Rat Liver Mitochondria. *J Biol Chem* 258:9477-9487.
(11) Izai K, Uchida Y, Orii T, Yamamoto S, Hashimoto T. (1992). Novel fatty acid β-oxidation enzymes in rat liver mitochondria. 1. Purification and properties of very-long-chain acyl-Coenzyme A dehydrogenase. *J Biol Chem* 267:1027-1033.
(12) Rozen R, Vockley J, Zhou L, Milos R, Willard J, Fu K, Vicanek C, Low-Nang L, Torban E, Fournier B. (1994). Isolation and expression of a cDNA encoding the precursor for a novel member (ACADSB) of the acyl-CoA dehydrogenase gene family. *Genomics* 24:280-287.
(13) Willard J, Vicanek C, Battaile K P, Vanveldhoven P P, Fauq A H, Rozen R, Vockley J. (1996). Cloning of a cDNA for short/branched chain acyl-coenzyme A dehydrogenase from rat and characterization of its tissue expression and substrate specificity. *Arch Biochem Biophys* 331:127-133.
(14) Nguyen T V, Andresen B S, Corydon T J, Ghisla S, Abd-El Razik N, Mohsen A W, Cederbaum S D, Roe D S, Roe C R, Lench N J, Vockley J. (2002). Identification of isobutyryl-CoA dehydrogenase and its deficiency in humans. *Mol Genet Metab* 77:68-79.
(15) Zhang J, Zhang W, Zou D, Chen G, Wan T, Zhang M, Cao X. (2002). Cloning and functional characterization of ACAD-9, a novel member of human acyl-CoA dehydrogenase family. *Biochem Biophys Res Commun* 297:1033-1042.
(16) Ikeda Y, Okamura-Ikeda K, Tanaka K. (1985). Spectroscopic analysis of the interaction of rat liver short chain, medium chain and long chain acyl-CoA dehydrogenases with acyl-CoA substrates. *Biochemistry* 24: 7192-7199.
(17) Ikeda Y, Hine D G, Okamura-Ikeda K, Tanaka K. (1985). Mechanism of action of short-chain, medium-chain, and long-chain acyl-CoA dehydrogenases: Direct evidence for carbanion formation as an intermediate step using enzyme-catalyzed C-2 proton/deuteron exchange in the absence of C-3 exchange. *J Biol Chem* 260:1326-1337.
(18) Mohsen, A.-W. and Vockley, J. (1995). High-level expression of an altered cDNA encoding human isovaleryl-CoA dehydrogenase in *Escherichia coli*. *Gene* 160:263-267.
(19) Matsubara, Y. Indo, Y., Naito, E., Ozasa, H., Glassberg, R., Vockley, J., Ikeda, Y., Kraus, J. (1989) Molecular cloning and nucleotide sequence of cDNAs encoding the precursors of rat long chain acyl-Coenzyme A, short chain acyl-Coenzyme A, and isovaleryl-Coenzyme A dehydrogenases. Sequence homology of four enzymes of the acyl-CoA dehydrogenase family *J Biol Chem* 267:16321-16331.

(20) Vockley, J., Mohsen, A.-W., Binzak, B., Willard, J. and Fauq, A. (2000). Mammalian branched-chain Acyl-CoA Dehydrogenases: Molecular cloning and characterization of the recombinant enzymes. *Methods Enzymol* 324:241-258.

(21) McKean, M. C., Frerman, F. E., and Mielke, D. M. (1979). General acyl-CoA dehydrogenase from pig liver. Kinetic and binding studies. *J Biol Chem* 254:2730-2735.

(22) Frerman, F. E., and Goodman, S. I. (1985). Fluorometric assay of acyl-CoA dehydrogenases in normal and mutant human fibroblasts. *Biochem Med* 33:38-44.

(23) Kim, J-J, Wang, M., Paschke, R. (1993). Crystal structures of medium-chain acyl-CoA dehydrogenase from pig liver mitochondria with and without substrate. *Proc Natl Acad Sci* USA 90:7523-7527.

(24) Schulz, H. (1974). Long chain enoyl coenzyme A hydratase from pig heart. *J Biol Chem* 249:2704-2709.

(25) Macheroux P, Sanner C, Büttner H, Kieweg V, Rüterjans H, and Ghisla S. (1997). Mediumchain acyl CoA dehydrogenase: evidence for phosphorylation. *Biol Chem.* 378: 1381-1385.

(26) Mohsen, A.-W. and Vockley, J. in (Ghisla, S., Kroneck, P., Macheroux, P. and Sund, H., eds.) Flavins and Flavoproteins 1999, Rudolf Weber, New York 1999, pp. 515-518.

(27) I. Nasser, A.-W. Mohsen, I. Jelesarov, J. Vockley, P. Macheroux, S. Ghisla, (2004). Thermal unfolding of medium-chain acyl-CoA dehydrogenase and iso(3) valeryl-CoA dehydrogenase: study of the effect of genetic defects on enzyme stability, *Biochim. Biophys. Acta* 1690: 22-32.

Various publications are cited herein, the contents of which are hereby incorporated by reference in their entireties.

What is claimed is:

1. A method for treating medium chain acyl-CoA dehydrogenase deficiency in a subject suffering therefrom comprising administering, to the subject, an effective amount of phenylbutyrate and/or another source of phenylacetate as a regular therapy regimen.

2. The method of claim 1, where phenylbutyrate is administered as a phenylbutyrate salt.

3. The method of claim 2, where the salt is sodium phenylbutyrate.

4. The method of claim 1, where triphenylbutyrylglycerol is administered to the subject as a source of phenylacetate.

5. The method of claim 1, where a mixture of sodium benzoate and sodium phenylacetate is administered to the subject as a source of phenylacetate.

6. A method for treating medium chain acyl-CoA dehydrogenase deficiency in a subject suffering therefrom comprising administering, to the subject, an effective amount of phenylbutyrate and/or another source of phenylacetate when the subject is at metabolic risk.

7. The method of claim 6, where the subject is at metabolic risk because of an infection.

8. The method of claim 6, where the subject is at metabolic risk because of a fasting interval.

9. The method of claim 6 where phenylbutyrate is administered as a phenylbutyrate salt.

10. The method of claim 9, where the salt is sodium phenylbutyrate.

11. The method of claim 6, where triphenylbutyrylglycerol is administered to the subject as a source of phenylacetate.

12. The method of claim 6, where a mixture of sodium benzoate and sodium phenylacetate is administered to the subject as a source of phenylacetate.

* * * * *